United States Patent [19]
Bark et al.

[11] Patent Number: 5,141,508
[45] Date of Patent: Aug. 25, 1992

[54] TISSUE EXPANDER

[75] Inventors: Jeffrey E. Bark, Paso Robles, Calif.; John E. Falk, Racine, Wis.

[73] Assignee: Medical Engineering Corporation, Racine, Wis.

[21] Appl. No.: 640,665

[22] Filed: Jan. 14, 1991

[51] Int. Cl.$^5$ .............................................. A61F 2/12
[52] U.S. Cl. .............................................. 623/8; 623/7
[58] Field of Search ........................................ 623/7, 8

[56] References Cited

U.S. PATENT DOCUMENTS

| | | | |
|---|---|---|---|
| 3,304,558 | 2/1967 | Mann | 623/7 |
| 3,516,414 | 6/1970 | Greenough | 623/7 |
| 3,663,968 | 5/1972 | Mohl et al. | 623/7 |
| 3,683,424 | 8/1972 | Pangman | 623/8 |
| 3,795,921 | 3/1974 | Zucher | 623/7 |
| 3,860,969 | 1/1975 | Arion | 623/8 |
| 4,263,682 | 4/1981 | Bejarano | 623/8 |

Primary Examiner—Randall L. Green
Assistant Examiner—G. Gualtieri
Attorney, Agent, or Firm—Stuart E. Krieger

[57] ABSTRACT

The tissue expander includes a shell with a base layer and an expansion layer that define an expansion chamber therebetween. A conduit or fill tube extends from the shell and is the sole source of communication with the expansion chamber. The base and expansion layers are thermoplastically joined together by a major seam and a minor seam. The major seam is substantially concealed within the expansion chamber whereas the minor seam defines a border portion of the expansion chamber and is not concealed. The tissue expander can be of any selected size and shape. The base layer can be made expandable along with the expansion layer or nonexpandable as desired.

12 Claims, 4 Drawing Sheets

TISSUE EXPANDER

BACKGROUND OF THE INVENTION

This invention relates to implantable devices which promote tissue growth or tissue expansion, and more particularly to a novel two-layer tissue expander that can be used for short or long term tissue expansion procedures.

The present invention, although primarily suitable for short term tissue expansion procedures that precede corrective or cosmetic surgery, may also be applied to longer term tissue expansion procedures that generally accompany reconstructive surgery.

Most tissue expanders, whether adapted for long term or short term expansion procedures, are usually made of silicone elastomers. The formation of a tissue expander from silicone can include a molding process as well as a bonding process using adhesives such as RTVs or unvulcanized sheets placed between surfaces to be bonded. The unvulcanized sheets are then baked or cured to complete the bond.

For example, U.S. Pat. No. 4,823,815 to Watson et al. shows a tissue expander device that includes a base layer, an expansion layer and peripheral washers that overlap and extend from the base layer and the expansion layer. The base and expansion layers and the overlapping washers which are formed of silicone are bonded together at their peripheries using RTV adhesives or a vulcanization process wherein unvulcanized sheets are baked or cured to complete the bond. The resulting structure includes an exposed circumferential edge which can lead to tissue trauma, especially if the device is used for long term implantation. In addition, the overlapping washers complicate the structure of the tissue expander and increase the manufacturing cost.

In a short term tissue expansion procedure also known as an intra-operative expansion procedure, a surgeon places a temporary expander in a subcutaneous pocket. The temporary expander is infused or inflated a predetermined amount to place the overlying tissue under tension. After several minutes the tissue expander is deflated and then subsequently reinflated. This expansion and deflation cycle is usually repeated several times during one sitting. When a surgeon has determined that the tissue has stretched sufficiently, the temporary expander is removed and a corrective or reconstructive surgery is performed which may include placement of a permanent implant or tissue expander. If either or both the temporary expander and permanent implant are formed of silicone, then the material costs can be relatively high.

It is thus desirable to provide a tissue expander that need not be vulcanized, baked or cured, can be used for short term or long term tissue expansion procedures, and reduces the prospect of tissue trauma.

OBJECTS AND SUMMARY OF THE INVENTION

Among the several objects of the invention may be noted the provision of a novel tissue expander, a novel tissue expander which is formed of a thermoplastic material, a novel tissue expander which includes thermoplastic bonding seams, a novel tissue expander having an expansion chamber in which a substantial portion of a shell seam is concealed within the expansion chamber, a novel tissue expander which can be used for short or long term use, a novel tissue expander which is substantially flat in an unexpanded condition, a novel tissue expander having an expansion layer and a base layer that are of substantially the same shape and area, a novel tissue expander which can be formed in a variety of selected shapes that include peripheries having curves and straight lines and a novel method of making a tissue expander.

Other objects and features of the invention will be in part apparent and in part pointed out hereinafter.

In accordance with one embodiment of the invention, the tissue expander includes a flexible shell having a base layer and an expansion layer that define an internal chamber. A fluid conduit that in several embodiments is disposed intermediate the base and expansion layer communicates with the expansion chamber. The fluid conduit can also be installed directly through the expansion layer.

In all embodiments of the invention a major thermoplastic seam or seal that extends around a major portion of the shell is entirely concealed within the expansion chamber. A minor thermoplastic seam or seal which extends around a minor portion of the shell defines a border portion of the expansion chamber.

The shell is preferably formed of thermoplastic material such as PVC material for short term usage or polyurethane material for long term usage. The base and expansion layers can have identical expansion characteristics or the base layer can be made relatively nonexpandable by use of a thicker or higher durometer material than that of the expansion layer. The base layer can also be formed of a relatively nonexpandable material or can include a fabric reinforcement such as Dacron mesh or a suitable known laminate of relatively nonexpandable material.

If desired, the tissue expander can be formed of two different materials, for example, the base can be formed of polyurethane and the expansion layer can be formed of PVC.

In making the tissue expander, a base layer and expansion layer of a shell construction are partially joined together by a first or major seam or seal which extends around the major portion of the shell. A conduit is joined to the shell construction and the base and expansion layers are turned inside out. In this manner the first or major seam is concealed intermediate the base and expansion layers, within an expansion chamber of the shell. A second or minor seam or seal is then provided to close the shell construction and seal the expansion chamber.

The concealed major seam of the shell, since it does not contact the tissue, reduces the prospect of tissue trauma to a patient during the tissue expansion procedure.

The invention accordingly comprises the constructions and method hereinafter described, the scope of the invention being indicated in the claims.

DESCRIPTION OF THE DRAWINGS

In the accompanying drawings,

FIG. 5a is a sectional view thereof after insertion of a conduit member;

Corresponding reference characters indicate corresponding parts throughout the several views of the drawings.

DETAILED DESCRIPTION OF THE INVENTION

Figure 1:
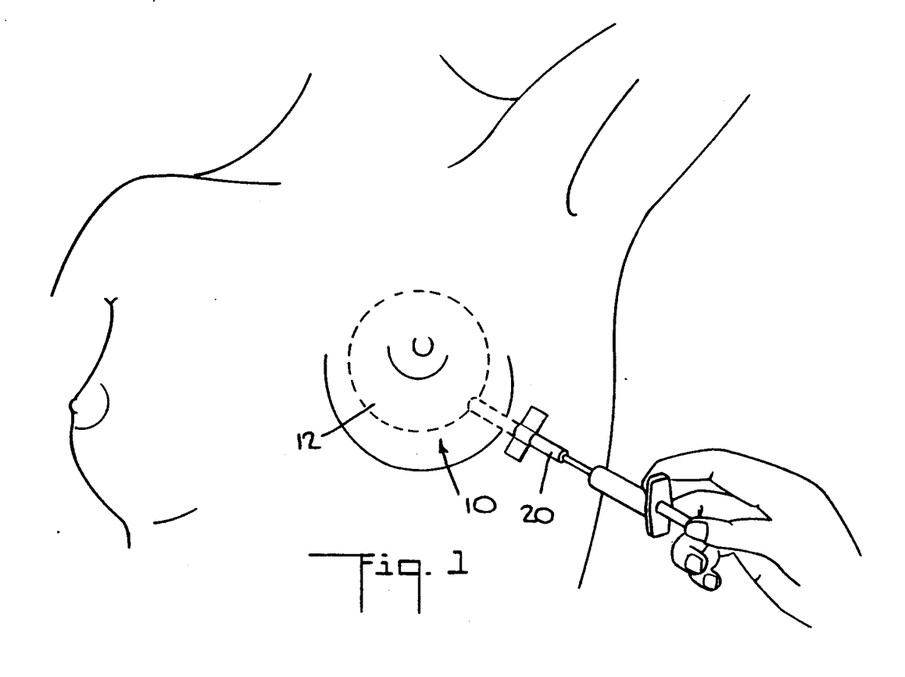
FIG. 1 is a simplified schematic pictorial view showing a tissue expander incorporating one embodiment of the invention, in an implanted position and being infused with fluid.
Figures 2, 3:
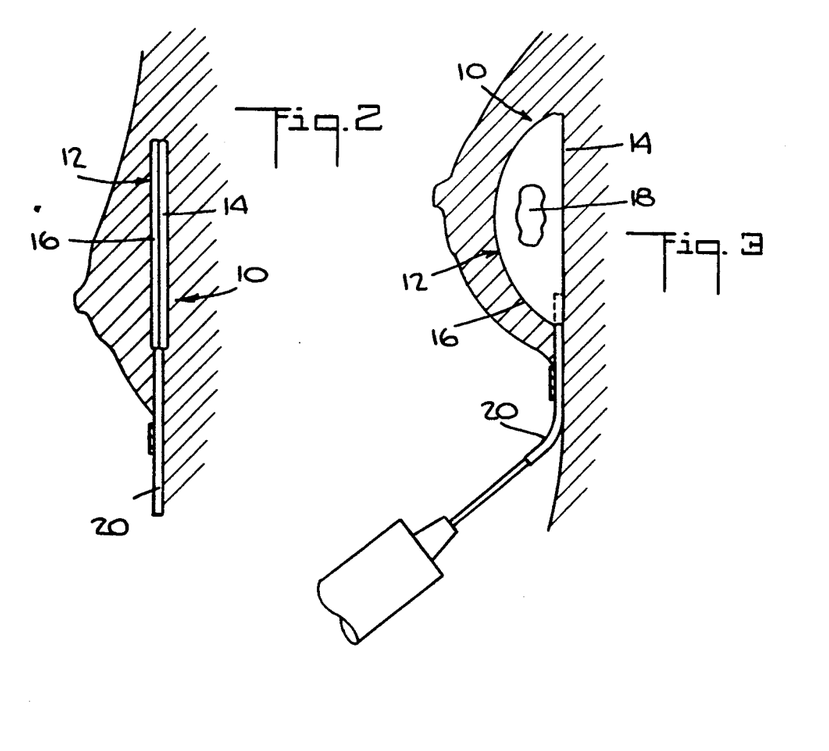
FIG. 2 is a simplified schematic side view thereof in an implanted condition prior to infusion of fluid therein.
FIG. 3 is a view similar to FIG. 2 after fluid is infused therein.

A tissue expander device incorporating one embodiment of the invention is generally indicated by the reference number 10 in FIGS. 1-3.

Referring to FIGS. 2-3, the tissue expander 10 includes a shell 12 having a base layer 14 and an expansion layer 16 joined together to define an expansion or fill chamber 18. A conduit 20 is joined to the shell 12 to provide fluid access to the fill chamber 18.

Unless otherwise indicated, the tissue expander 10 is made from a suitable known biocompatible thermoplastic material such as polyvinyl chloride (PVC), for example, for short term usage or polyurethane, for example, for long term usage. However, a tissue expander constituted as a combination of polyurethane and PVC is also contemplated. Either of these materials can be solvent bonded, thermoplastically welded as by radio frequency (R.F.) sealing or heat sealing, and thus require less time and equipment for their manufacture than devices formed of silicone elastomers.

Figures 4, 5, 6, 6A, 7, 8, 9, 9A:
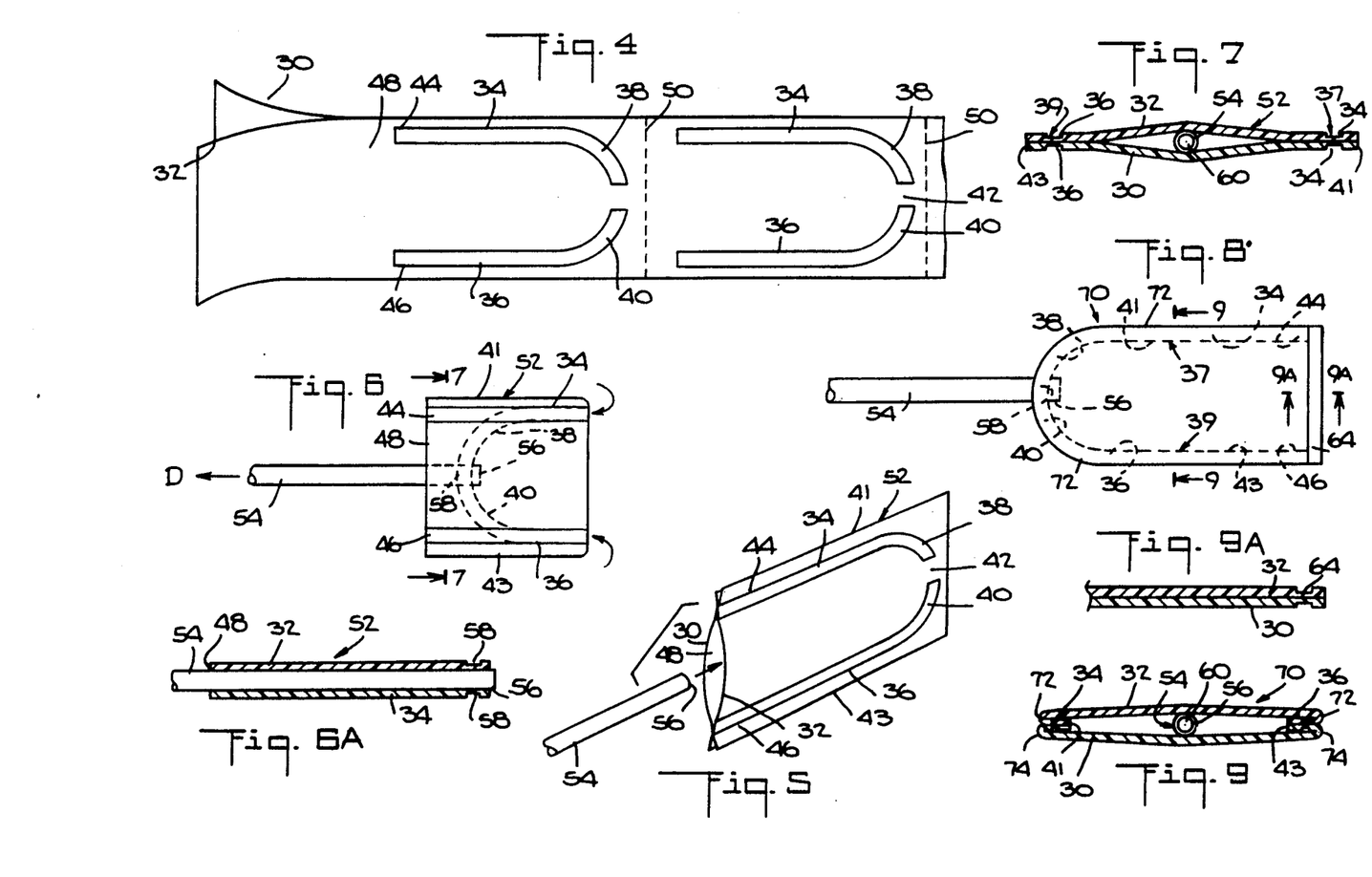
FIG. 4 is a simplified schematic plan view of a tissue expander incorporating a further embodiment of the invention showing the shell thereof in a preliminary manufacturing stage.
FIG. 5 is a simplified schematic perspective view thereof at a further advanced manufacturing stage.
FIG. 6 is a simplified schematic plan view thereof in a still further advanced manufacturing stage wherein the shell is being turned inside out.
FIG. 6a is a sectional view of the conduit provided with a thermoplastic weld.
FIG. 7 is a sectional view taken on the line 7—7 of FIG. 6.
FIG. 8 is a simplified schematic plan view of the completed tissue expander.
FIG. 9 is a sectional view taken on the line 9—9 of FIG. 8.
FIG. 9a is a fragmentary sectional view taken on the line 9a—9a of FIG. 8.

For example, referring to FIG. 4, two sheets 30 and 32 of extruded polyurethane or PVC film are placed one on top of the other. Elongated heat seals, solvent bonds or R.F. welds 34 and 36 which can be generally referred to as thermoplastic welds are provided to bond the sheets 30 and 32 together thereby defining bonded portions 37 and 39 (FIG. 7) having edges 41 and 43. Subsequent portions of this description refer specifically to heat seals for purposes of simplicity.

Referring to FIG. 4, the thermoplastic welds 34 and 36 have respective curved end portions 38 and 40 spaced from each other to define an unbonded area 42. The thermoplastic welds 34 and 36 also have corresponding straight end portions 44 and 46, with an intermediate unbonded section 48. Score lines 50 are provided at spaced intervals in the sheets 30 and 32 and a repeating pattern of the thermoplastic welds 34 and 36 can be provided on the sheets 30 and 32 intermediate consecutively spaced score lines 50.

Referring to FIG. 5, an expander blank 52 is cut from the sheets 30 and 32 along a score line 50 and at the straight end portions 44 and 46. A conduit member 54 is inserted between the sheets 30 and 32 of the expander blank 52 through the unbonded sections 48 and 42. An end portion 56 of the conduit 54 projects beyond the expander blank 52 a predetermined amount. A thermoplastic weld 58 (FIG. 6a) is provided over the conduit 54 at the unbonded section 42 of the sheets 30 and 32 to form a continuation between the thermoplastic welds 34 and 36 at the curved end portions 38 and 40. The thermoplastic weld 58 extends 360° around the conduit 54 to assure that there is a leak-tight seal between the sheets 30 and 32 and the conduit 54.

Referring to FIG. 6, the expander blank 52 is turned inside out by pulling on the conduit 54, now affixed at the thermoplastic weld 58, in the direction D in FIG. 6. In this manner the end of the expander blank having the curved end portions 38 and 40 of the thermoplastic welds 34 and 36 is drawn toward and through the unbonded section 48. It should be noted that before the expander blank 52 is turned inside out, the edge portions 41 and 43 can be finished or trimmed closely to the respective seals 34 and 36. Also, if desired, the thermoplastic welds 34 and 36 can be located at the edge portions 41 and 43 to avoid any need for a trimming operation.

As most clearly shown in FIG. 9, with the expander blank 52 turned inside out, the seals 34 and 36 and the edges 41 and 43 are concealed between the sheets 30 and 32 since the bonded portions 37 and 39 are sandwiched between said sheets. Referring to FIGS. 8 and 9, the end portion 56 of the conduit 54 is now located intermediate the sheets 30 and 32 and the conduit 54 extends away from the curved end portions 38 and 40 of the thermoplastic welds 34 and 36.

After the expander blank 52 has been turned inside out, a thermoplastic weld 64 (FIGS. 8 and 9) is provided to join the unbonded section 48 of the sheets 30 and 32. The thermoplastic weld 64 extends across and overlaps the straight end portions 44 and 46 of the thermoplastic welds 34 and 36 that are disposed intermediate the sheets 30 and 32. The thermoplastic weld 64 also forms a leak-tight seal with the bonded portions 37 and 39. An expansion or fill chamber 68 is thus defined between the sheets 30 and 32 with the resulting structure constituting a tissue expander 70 as shown in FIG. 8.

Referring to FIGS. 8 and 9, a major seam or seal portion of the tissue expander 70 defined by the seams 34, 36 and 58 has smooth folded outwardly exposed curved surfaces 72 and 74 which are free of any finished or unfinished edges, and define a major border portion of the fill chamber 68. The sheets 30 and 32 can be respectively characterized as the base and expansion layers of the tissue expander 70. The base and expansion layers 30 and 32 can be formed of the same material having the same expansion characteristics. For example, for a short term tissue expander, the material used can be PVC or polyurethane having a thickness of approximately 0.125 millimeters. For a relatively long term tissue expander the material used can be polyurethane having a thickness of approximately 0.2 millimeters.

If desired, the base and the expansion layers 30 and 32 can have different expansion characteristics. For example, the base layer 30 in a short term tissue expander can be formed of polyurethane with a durometer of 80A which is relatively nonexpandable when compared to a lower durometer such as 40A. For a long term tissue expander the base layer 30 can be formed of high durometer polyurethane which is relatively nonexpandable.

As another option, the base layer 30 can be thicker than the expansion layer to render the base layer relatively nonexpandable. For example, the base layer thickness can be approximately two times the thickness of the expansion layer.

The inflated or expanded shape of the tissue expander 70 is determined by the type of material used for the base layer and the expansion layer, the thickness of the respective materials, and the geometrical configuration of the fill chamber. The tissue expander 70 may be rolled or folded to a small configuration to permit placement through a relatively small incision.

It should be noted that because the finished or unfinished edges 41 and 43 of the tissue expander 70 are concealed within the expansion chamber 68 and the major peripheral portion of the chamber 68 has the folded over smooth curved surfaces 72 and 74, the prospect of tissue trauma is substantially minimized after implantation of the tissue expander 70.

In using the tissue expander 70, fluid is infused into the expansion chamber 68 through the lumen 60 of the conduit 54 in any suitable known manner, including use of a syringe such as 98 (FIGS. 1 and 2), for example. If the tissue expander 70 is intended for long term usage, a fill port such as shown in U.S. Pat. No. 4,802,885 can be used. However, for short term usage of the tissue expander 70, a fill port is generally not necessary and a syringe can be used to infuse fluid directly into the conduit 54 in a manner such as shown in FIGS. 2 and 3.

A known normally closed valve (not shown) can be provided in the conduit 54 which is adapted to open only in the presence of the syringe. Leak-tight integrity of the tissue expander 80 after the syringe 98 is withdrawn is thus assured.

Figures 10, 10A, 11, 12, 13, 14, 14A:
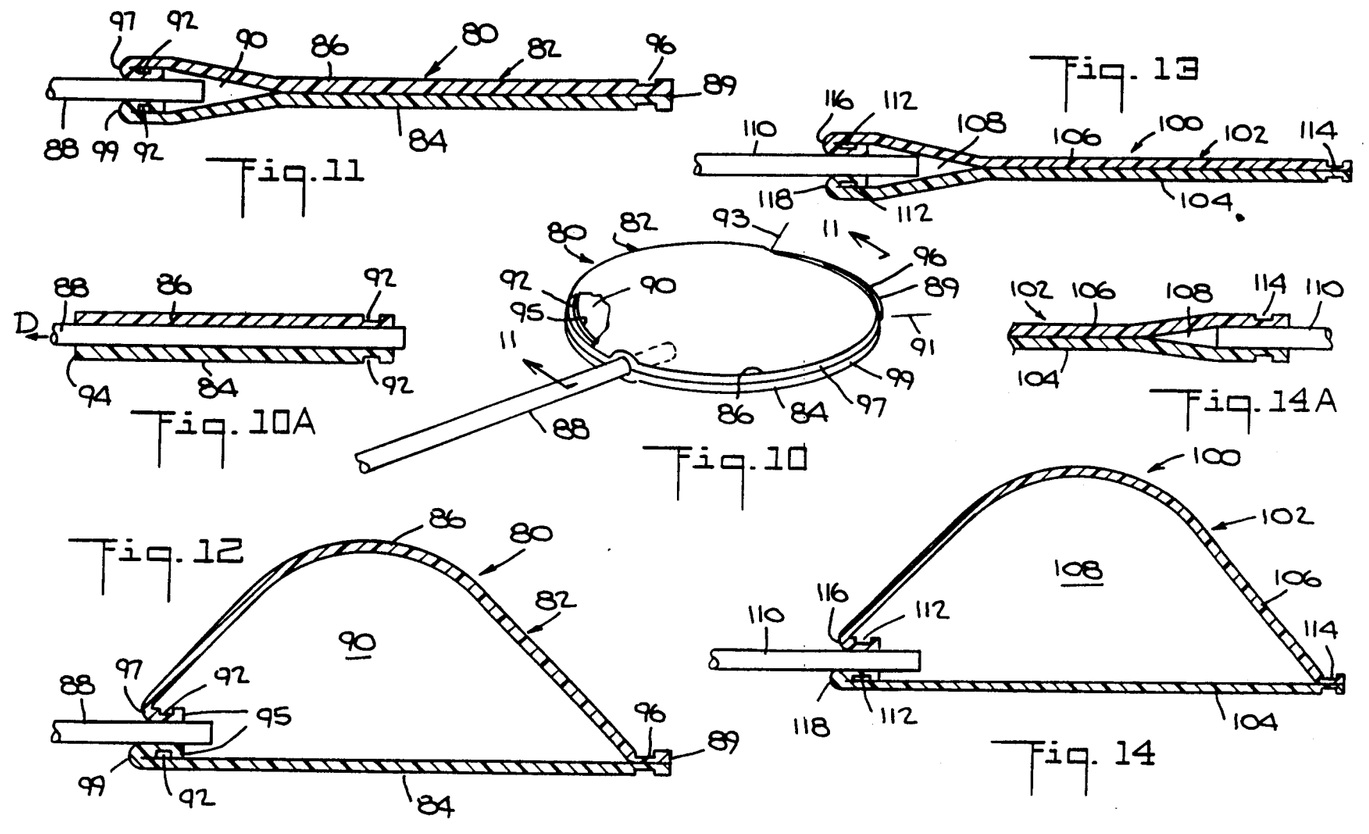
FIG. 10 is a simplified schematic perspective view of another embodiment thereof.
FIG. 10a is a sectional view thereof showing the shell in a preliminary manufacturing stage, before being turned inside out.
FIG. 11 is an enlarged sectional view of the finished tissue expander, taken on the line 11—11 of FIG. 10, wherein the tissue expander is in a collapsed uninflated condition.
FIG. 12 is a sectional view thereof in an inflated expanded condition.
FIG. 13 is an enlarged sectional view of another embodiment thereof in a collapsed uninflated condition.
FIG. 14 is a sectional view thereof in an inflated expanded condition.
FIG. 14a is a fragmentary sectional view showing an alternative construction thereof.

Another embodiment of the tissue expander is generally indicated by the reference number 80 in FIG. 10. The tissue expander 80 includes a shell 82 having a base layer 84 and an expansion layer 86. The base layer 84 is of a thicker material than the expansion layer 86 to assure that the base layer is substantially nonexpandable relative to the expansion layer 86, as shown in FIG. 12. A conduit 88 is disposed between the base and expansion layers 84 and 86 for communication with an expansion chamber 90 defined between the base and expansion layers.

The tissue expander 80 can be made in a manner similar to that previously described for the tissue expander 70. For example, a major thermoplastic weld 92 which is concealed within the expansion chamber 90 corresponds to the thermoplastic welds 34, 36 and 58 of the tissue expander 70. Referring to FIGS. 10 and 12, the major thermoplastic weld 92 overlaps the conduit 88 and extends approximately 270° around the shell 82 in a clockwise direction from the radial reference 91 to the radial reference 93. A second minor thermoplastic weld 96, which is not concealed within the expansion chamber 90 and corresponds to the thermoplastic weld 64 of the tissue expander 70, extends approximately 90° around the shell 82 in a clockwise direction from the radial reference 93 to the radial reference 91 substantially opposite the conduit 88. The minor thermoplastic weld 96 does not project into the expansion chamber 90 but defines a peripheral border portion of such expansion chamber as most clearly shown in FIG. 12.

Referring to FIG. 10a, in manufacturing the tissue expander 80, the base and expansion layers 84 and 86 are bonded together at the major thermoplastic weld 92 leaving a minor opening 94 that is eventually sealed by the minor thermoplastic weld 96. The conduit 88 is thus sandwiched between the layers 84 and 86 and extends through the minor opening 94. The layers 84 and 86 are then turned inside out in a manner similar to that shown and described in FIG. 6. Thus the conduit 88 is pulled in the direction D (FIG. 10a) such that it draws the bonded layers 84 and 86 at the major thermoplastic weld 92 through the minor opening 94. The finished or unfinished edges 95 of the layers 84 and 86 at the major thermoplastic weld 92 are thereby concealed within the fill chamber 90 as shown in FIGS. 10, 11 and 12. A major outer peripheral portion of the tissue expander shell 82 proximate the major thermoplastic weld 90 has folded over smooth curved surfaces 97 and 99, thereby minimizing the prospect of tissue trauma after implantation of the tissue expander 70.

The minor opening 94 is thermoplastic welded by the minor thermoplastic weld 96 which overlaps the ends of the major thermoplastic weld 92 at the radial references 91 and 93 such that the fill chamber 90 is entirely sealed except for the access provided through the conduit 88. The minor thermoplastic weld 96 has an exposed edge 89 which can be finished or unfinished.

A further embodiment of the tissue expander is generally indicated by the reference number 100 in FIGS. 13 and 14. The tissue expander 100 includes a shell 102 with a base layer 104 and an expansion layer 106 of substantially the same thickness. An expansion chamber 108 is defined between the base and expansion layers 104 and 106. However, the base layer 104 is of a higher durometer material than the expansion layer 106 and is relatively nonexpandible in comparison with the expansion layer 106. For example, the durometer of the base layer 104 can be approximately 80A durometer and the durometer of the expansion layer 106 can be approximately 50A durometer.

A conduit member 110 is disposed intermediate the base and expansion layers 104 and 106 in a manner similar to that previously described for the tissue expanders 10, 70 and 80. The shell 102 is also characterized by a major thermoplastic weld 112 and a minor thermoplastic weld 114 which correspond to the major and minor thermoplastic welds 92 and 94 of the tissue expander 80. The shell also includes folded over smooth outer curved surfaces 116 and 118 that correspond to the folded over surfaces 97 and 99 of the tissue expander 70.

The tissue expander 100 is formed and assembled in a manner similar to that previously described for the tissue expander 80 wherein the major thermoplastic weld 112 extends along an arc of approximately 270° and is disposed internally of the expansion chamber 108 whereas the minor thermoplastic weld 114 extends along an arc of approximately 90° and defines a border portion of the expansion chamber 108.

Referring to FIG. 14a, it should also be noted that the conduit 110 can exit through the minor seam 114 and thus be sandwiched between unfolded base and expansion layers 104, 106, rather than the shell 102 being folded back on itself around the conduit 110. This alternative construction wherein the conduit is sandwiched between unfolded base and expansion layers can be used for any of the embodiments disclosed herein. Thus, in the alternative construction, the partially bonded shell is turned inside out in any suitable known manner and thereafter the conduit is bonded to the shell between the unfolded base and expansion layers.

The tissue expander 100 is used in a manner similar to that previously described for the tissue expanders 10, 70 and 80.

Figure 15:
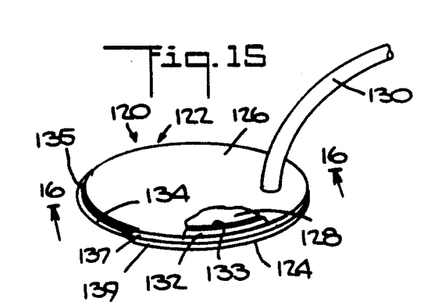
FIG. 15 is a simplified perspective view of another embodiment thereof.
Figure 16:
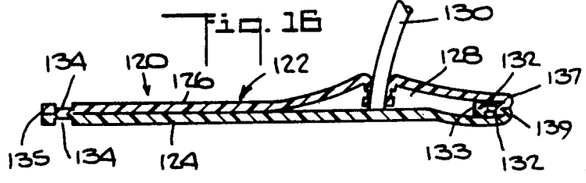
FIG. 16 is a sectional view thereof, taken on the line 16—16 of FIG. 15, showing the tissue expander in a collapsed uninflated condition.

A further embodiment of the tissue expander is generally indicated by the reference number 120 in FIG. 15. The tissue expander 120 includes a shell 122 with a base layer 124, an expansion layer 126 and an expansion chamber 128 defined therebetween. The base and expansion layers 124 and 126 can be formed of the same material with equal expansible characteristics.

A conduit 130 has a free end 131 joined to the shell 122 through the expansion layer 126 for communication with the expansion chamber 128. Preferably the free end 131 of the conduit 130 has rounded and finished edges. The shell 122 includes a major thermoplastic weld 132 joining the base and expansion layers 124, 126 along an arc of approximately 270° and a minor thermoplastic weld 134 joining such base and expansion layers 124 and 126 along an arc of approximately 90°. The major thermoplastic weld 132 and its associated edge 133 are concealed within the expansion chamber 128 whereas the minor thermoplastic weld 134 and its associated external edge 135 define a border portion of the expansion chamber 128. The shell 122 also includes folded over smooth outer curved surfaces 137 and 139 that correspond to the folded over surfaces 97 and 99 of the tissue expander 70.

It should be noted that prior to joining of the base and expansion layers 124 and 126 together at the minor thermoplastic weld 134, the conduit 130 extends through a minor unbonded section (not shown) that is eventually closed by the thermoplastic weld 134. The base and expansion layers 104 and 106 are thus turned inside out in a manner similar to that previously described for the tissue expanders 70 and 80 by pulling the conduit 130 and the major bonded section at the major thermoplastic weld 132 through the minor unbonded section (not shown). The shell 122 is thereafter thermoplastic bonded at the minor seam 134 in a manner similar to that previously described.

Figure 17:
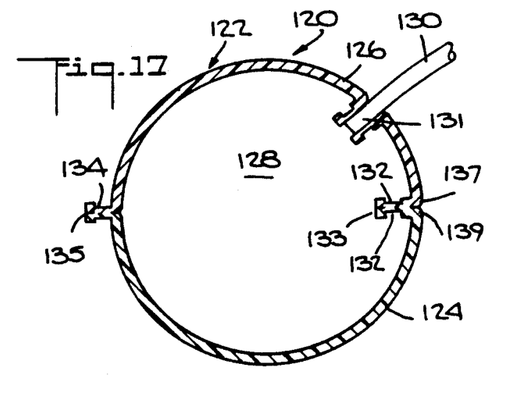
FIG. 17 is a sectional view thereof showing the tissue expander in an inflated expanded condition.

Since the base layer 124 and the expansion layer 126 have similar expansibility characteristics, the tissue expander 120 is freely expandable to a substantially spherical shape as shown in FIG. 17.

The tissue expander 120 is used in a manner similar to that previously described, and as with all the embodiments disclosed herein, can be used for long term or short term tissue expansion depending upon whether the tissue expander is formed of PVC or polyurethane.

Figure 18:
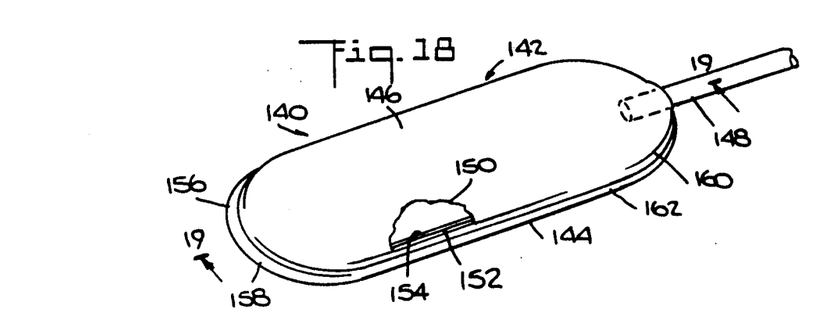
FIG. 18 is a simplified perspective view of another embodiment of the invention.
Figure 19:
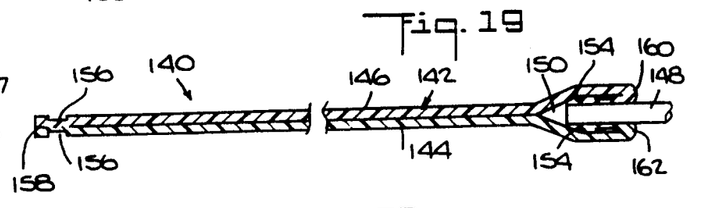
FIG. 19 is a sectional view thereof, taken on the line 19—19 of FIG. 18, showing the tissue expander in a collapsed uninflated condition; and, FIG. 20 is an enlarged sectional view thereof in an inflated expanded condition.
Figure 20:
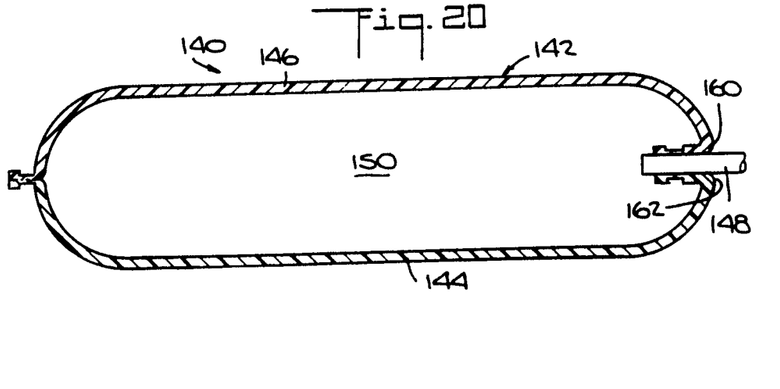

A still further embodiment of the tissue expander is generally indicated by the reference number 140 in FIGS. 18-20. The tissue expander 140 includes a shell 142, a base layer 144 and an expansion layer 146. A conduit member 148 is disposed intermediate the base and expansion layers 144 and 146 for communication with an expansion chamber 150 defined between the base and expansion layers.

The tissue expander 140 is generally elliptical-shaped in plan view and the base and expansion layers 144, 146 have similar expansion properties.

The shell 142 is provided with a major thermoplastic weld 152 having an associated edge 154 that is concealed inwardly of the expansion chamber 150 and a minor thermoplastic weld 156 with an associated external edge 158 that defines a border portion of the expansion chamber 150. The thermoplastic weld 152 corresponds to the thermoplastic welds 34, 36 and 58 of the tissue expander 70 and the thermoplastic weld 154 corresponds to the thermoplastic weld 64 of the tissue expander 70. The shell 142 also includes folded over smooth outer curved surfaces 160 and 162 that correspond to the folded over surfaces 97 and 99 of the tissue expander 70.

The tissue expander 140 is formed in a manner similar to that previously described for the tissue expander 70 and the minor thermoplastic weld 156 extends a predetermined minor width, such that before the thermoplastic weld 156 is applied, the tissue expander shell 142 can be turned inside out through the unbonded minor width. The tissue expander 140 is used in a manner similar to that previously described for the tissue expanders 10, 70, 80 and 100.

In some instances it may be desirable that the concealed inwardly extending thermoplastic weld be a minor seam and the outwardly extending thermoplastic weld be a major seam.

As will be apparent to those skilled in the art, the tissue expanders of the present invention can be formed in any selected shape or size, with one or both layers being expansible. The physical characteristics and chemical makeup of the expansible layer can also be controlled in known fashion to control the shape of the expansible layer. Thus, for example, the expansible layer can be made of varying thickness such that selected portions of the expansible layer are relatively more expansible than other portions thereof. Chemical characteristics of the base layer can be controlled as by durometer control and structural makeup to limit the expansibility of the base layer.

Some advantages of the present invention evident from the foregoing description include a tissue expander having bonded seams or joints that do not require curing, baking or vulcanization, and a tissue expander capable of being used for short or long term usage depending upon the material makeup of the device. A further advantage is that the tissue expander is less likely to cause tissue trauma than other known tissue expanders with fully exposed edges since a major portion of the circumferential periphery of the shell has a concealed edge.

Manufacture of the present tissue expander is substantially less expensive than tissue expanders which are constituted of silicone materials which require adhesives and the use of unvulcanized sheets between surfaces to be bonded. The thermoplastic materials which can be used to constitute the present tissue expander may be solvent bonded, R.F. sealed or heat sealed, all requiring less time and equipment than the silicone elastomers. Since the present tissue expander can be made in a simpler manner than expanders formed of silicone elastomers, a designer has greater flexibility in developing a form which can be closely correlated with the desired function of the tissue expander. A further advantage is that thermoplastic materials are generally much less expensive than silicone elastomers and have superior mechanical and physical properties than those of silicone elastomers resulting in a more durable tissue expander device.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A tissue expander for implantation in a patient to promote tissue growth comprising, a flexible shell having a base layer and an expansion layer defining an internal chamber, said base layer and said expansion layer having corresponding peripheries, a first portion of said corresponding peripheries being bonded together to form a first seam portion, said first seam portion being disposed inside said chamber, a second portion of said corresponding peripheries being bonded together to form a second seam portion, said second seam portion defining a border of said chamber, said first seam portion being of greater length than said second seam portion, and a fill tube joined to said shell between said base layer and expandable layer.

2. A tissue expander for implantation in a patient to promote tissue growth comprising a flexible shell having a base layer and an expansion layer defining an internal chamber, said base layer being formed of a relatively high durometer material and said expandable layer being formed of a relatively low durometer material, said base layer and said expansion layer being of substantially the same shape and area such that said shell has a substantially flat collapsed condition when said chamber is empty, said shell having first and second peripheral seams joining said base layer and said expansion layer, said first peripheral seam being disposed inside said chamber and said second peripheral seam defining a border portion of said chamber.

3. A tissue expander as claimed in claim 2 wherein said base layer is thicker than said expandable layer.

4. A tissue expander for implantation in a patient to promote tissue growth comprising, a flexible shell having a base layer and an expansion layer defining an internal chamber, said base layer and said expansion layer having corresponding peripheries, a first portion of said corresponding peripheries being bonded together to form a first seam portion, said first seam portion being disposed inside said chamber, a second portion of said corresponding peripheries being bonded together to form a second seam portion, said second seam portion defining a border of said chamber, said second seam portion being of greater length than said first seam portion, and a fill tube joined to said shell between said base layer and expandable layer.

5. A tissue expander for implantation in a patient to promote tissue growth comprising, a flexible shell having a base layer and an expansion layer defining an internal chamber, said base layer and said expansion layer having corresponding peripheries of circular shape, a first portion of said corresponding peripheries being bonded together to form a first seam portion, said first seam portion being disposed inside said chamber, a second portion of said corresponding peripheries being bonded together to form a second seam portion, said second seam portion defining a border of said chamber, and a fill tube joined to said shell between said base layer and expandable layer.

6. A tissue expander for implantation in a patient to promote tissue growth comprising, a flexible shell having a base layer and an expansion layer defining an internal chamber, said base layer and said expansion layer having corresponding peripheries of elliptical shape, a first portion of said corresponding peripheries being bonded together to form a first seam portion, said first seam portion being disposed inside said chamber, a second portion of said corresponding peripheries being bonded together to form a second seam portion, said second seam portion defining a border of said chamber, and a fill tube joined to said shell between said base layer and expandable layer.

7. A tissue expander for implantation in a patient to promote tissue growth comprising, a flexible shell having a base layer and an expansion layer defining an internal chamber, said base layer and said expansion layer having corresponding peripheries, a first portion of said corresponding peripheries being bonded together to form a curved first seam portion, said first seam portion being disposed inside said chamber, a second portion of said corresponding peripheries being bonded together to form a straight second seam portion, said second seam portion defining a border of said chamber, and a fill tube joined to said shell between said base layer and expandable layer.

8. A tissue expander for implantation in a patient to promote tissue growth comprising, a flexible shell having a base layer and an expansion layer defining an internal chamber, said base layer and said expansion layer having corresponding peripheries, a first portion of said corresponding peripheries being bonded together to form a curved first seam portion, said first seam portion being disposed inside said chamber, a second portion of said corresponding peripheries being bonded together to form a curved second seam portion, said second seam portion defining a border of said chamber, and a fill tube joined to said shell between said base layer and expandable layer.

9. A tissue expander for implantation in a patient to promote tissue growth comprising, a flexible shell having a base layer and an expansion layer defining an internal chamber, said base layer being formed of an expandable material that expands with said expansion layer, said base layer and said expansion layer having corresponding peripheries, a first portion of said corresponding peripheries being bonded together to form a first seam portion, said first seam portion being disposed inside said chamber, a second portion of said corresponding peripheries being bonded together to form a second seam portion, said second seam portion defining a border of said chamber, and a fill tube joined to said shell between said base layer and expandable layer.

10. A tissue expander for implantation in a patient to promote tissue growth comprising, a flexible shell having a base layer and an expansion layer defining an internal chamber, said base layer being formed of a non-expandable material that does not expand with said expansion layer, said base layer and said expansion layer having corresponding peripheries, a first portion of corresponding peripheries being bonded together to form a first seam portion, said first seam portion being disposed inside said chamber, a second portion of said corresponding peripheries being bonded together to form a second seam portion, said second seam portion defining a border of said chamber, and a fill tube joined to said shell between said base layer and expandable layer.

11. A tissue expander as claimed in claim 10 wherein said base layer is thicker than said expandable layer such that the base layer is relatively nonexpandable relative to said expansion layer.

12. A tissue expander as claimed in claim 10 wherein said base layer is formed of a relatively high durometer material and said expandable layer is formed of a relatively low durometer material.

* * * * *